United States Patent
Sha et al.

(10) Patent No.: US 8,168,282 B2
(45) Date of Patent: May 1, 2012

(54) TRIMETHINE CYANINE COMPOUNDS, THEIR PREPARATION AND THEIR USE

(75) Inventors: Chin Kang Sha, Hsinchu (TW); Cheng Fen Yang, Hsinchu (TW); Hsin Jen Lee, Hsinchu (TW)

(73) Assignee: Orgchem Technologies, Inc., Hsinchu (TW)

( * ) Notice: Subject to any disclaimer, the term of this patent is extended or adjusted under 35 U.S.C. 154(b) by 723 days.

(21) Appl. No.: 12/253,993

(22) Filed: Oct. 19, 2008

(65) Prior Publication Data

US 2010/0068442 A1  Mar. 18, 2010

(30) Foreign Application Priority Data

Oct. 24, 2007  (TW) .................. 96139809 A

(51) Int. Cl.
  *B32B 3/02* (2006.01)
  *G11B 7/24* (2006.01)
(52) U.S. Cl. ............. 428/64.8; 428/64.4; 430/270.21; 548/427; 548/455; G9B/7.151
(58) Field of Classification Search ............. 428/64.4, 428/64.8; 430/270.2, 270.21; 548/455, 457, 548/427; G9B/7.151
See application file for complete search history.

(56) References Cited

U.S. PATENT DOCUMENTS 3,714,187 A * 1/1973 Ono et al. ............... 548/409
3,923,824 A * 12/1975 Ono et al. ............... 548/240

FOREIGN PATENT DOCUMENTS

GB  1274591 A  *  5/1972
JP  03081278 A  *  4/1991

OTHER PUBLICATIONS

Flerova, A. et al. "Synthesis and Properties of Photochromic Bisindolinospiropyrans", Chemistry of Heterocyclic Compounds, 1973, vol. 9, p. 1476-1482.*

* cited by examiner

*Primary Examiner* — Gerard Higgins
(74) *Attorney, Agent, or Firm* — Muncy, Geissler, Olds & Lowe, PLLC

(57) ABSTRACT

The present invention relates to a trimethine cyanine represented by the formula (1):

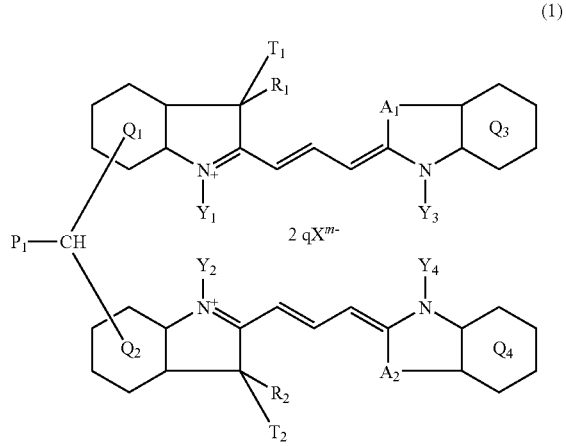

(1)

wherein each of the symbols are defined in the specification. The present invention also relates to a use of the above dimeric trimethine cyanine compound as a dye, which is used in an optic element, particularly a high density recordable optical media.

7 Claims, No Drawings

TRIMETHINE CYANINE COMPOUNDS, THEIR PREPARATION AND THEIR USE

FIELD OF THE INVENTION

The present invention relates to trimethine cyanine compounds, their preparation and their use as dyes which are applied to various optical elements, especially to optical recording medium recorded by laser beam.

BACKGROUND OF THE INVENTION

With rapid progress in digital world, recording medium of large storage capacity, small in size, and low production cost is demanded. Among them, optical recording medium is the most popular one due to its large storage capacity. Such optical recording medium is commercial available as an optical disc which is recorded by laser beam. Such an optical recording medium is mainly classified into two kinds, one is a recordable optical disc on which information can be recorded and played and the other one is a rewritable optical disc on which information can be recorded, erased, and played. The recordable optical disc is much popular due to its low cost and excellent stability.

Regarding the recordable optical disc, it is further classified into DVD-R and CD-R, and the storage capacity for DVD-R is about 7 times of that for CD-R. The wavelength of the laser for recording and playing DVD-R is about 650 nm so that an organic dye having strong absorbance in the range of 550-620 nm can be used as a recording layer for DVD-R disc. For using in optical disc, the dye is required to have a good solubility in organic solvent, especial in alcohol solvents, an excellent film-forming ability, a good stability, and a high reflectivity when forming into a film. Currently, the DVD-R disc has advanced to high writing speed, for example, increased from 1×~8× to 12×~16×.

Properties of the recording material in the recording layer are more important when the recording disc is recorded at a high writing speed. The laser power for recording would be increased when the recording is carried out at a high writing speed in order to record information on the disc in short time. However, the larger laser pulse will result in expending of pit laterally when it illuminates on the disc, even damage the trench on the disc or destroy the information recorded on the disc. However, in case of that the writing is carried out at a high writing speed, if the recording material in the recording layer can be written at a low laser power, the limitation on recording machines and recording mechanism will be eliminated. A low jitter value of the recording material is also required. Therefore, to work well at high writing speed is to develop a novel recording material which possesses the following properties required in high writing speed: low burning power, low signal jitter, good film-forming ability, be soluble in the used solvent, and low exothermic heat.

There are several dyes used in recording material for optical recording medium currently, one of them is a cyanine compound. The cyanine compound is the first one successfully used as recording material in CD-R optical disc, and thus various cyanine derivatives have been widely developed and used as recording material in DVD-R optical disc, for example, those disclosed in Taiwan Patent Publication No. 591646, Taiwan Unexamined Patent Publication Nos. 200523917, 200306334, 200508325, 200519166, 200608384, 200613409, 200621710, and WO 2006/123807, and EP 154723A2. Physical properties of the cyanine derivatives can be modified by substituting functional groups on the molecular when using in recording material on optical recording medium, such as changing the light-absorbing wavelength, changing decomposing temperature, and endothermic and/or exothermic decomposition. However, such physical properties are not necessary relevant to the molecular structure and are screened certainly by experiments to select the suitable ones.

SUMMARY OF THE INVENTION

To resolve the above problems, the present invention provides a trimethine cyanine compound which is used as an optical recording material for writable DVD-R disc (i.e. recordable optical disc) written at a high writing speed.

The trimethine cyanine compound of the present invention (hereinafter sometimes refers to "cyanine compound" briefly) can be used for forming optical recording layer in an optical recording medium and can provide excellent thermal decomposability and use in high speed writable disc.

The present invention thus relates to:
1) A trimethine cyanine compound represented by the formula (1):

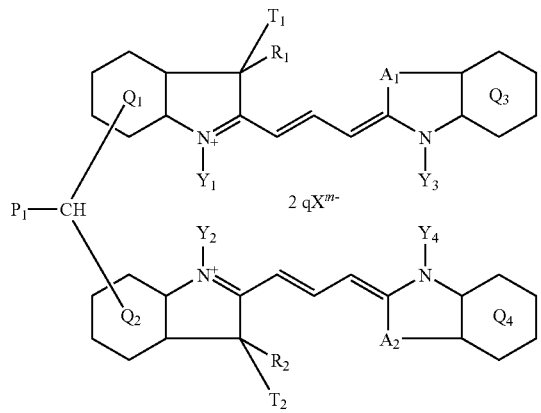

(1)

wherein:
$Q_1$, $Q_2$, $Q_3$, and $Q_4$ are the same or different and each represents a substituted or unsubstituted benzene ring or naphthalene ring;

$P_1$ is a hydrogen atom or an organic group having 1 to 18 carbon atoms;

$A_1$ and $A_2$ are the same or different and each represents groups of formula

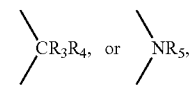

an oxygen atom, or a sulfur atom;

$Y_1$, $Y_2$, $Y_3$, and $Y_4$ are the same or different and each represents an organic group having 1 to 18 carbon atoms;

$T_1$ and $T_2$ are the same or different and each represents a substituted or unsubstituted benzyl group, a substituted or unsubstituted allyl group, or a substituted or unsubstituted propargyl group;

$R_1$, $R_2$, $R_3$, $R_4$, and $R_5$ are the same or different and each represents a hydrocarbon group having 1-18 carbon atoms, which is substituted or unsubstituted; or $R_3$ and $R_4$ is bonded together to form a 3- to 6-member carbon ring which is further optionally fused with a benzene ring;

$X^{m-}$ represents a counterion having m valence;

m represents an integral of 1, 2, or 3;

q represents a coefficient for maintaining charge neutrality.

2) The trimethine cyanine compound according to 1), which is the compound represented by the following formula (2):

(2)

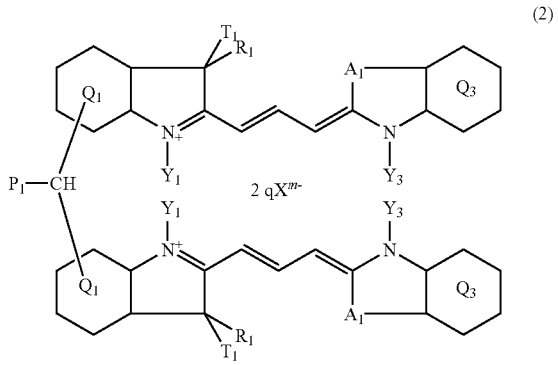

wherein each symbols are defined as above.

3) The trimethine cyanine compound according to 2), which is the compound represented by the following formula (3):

(3)

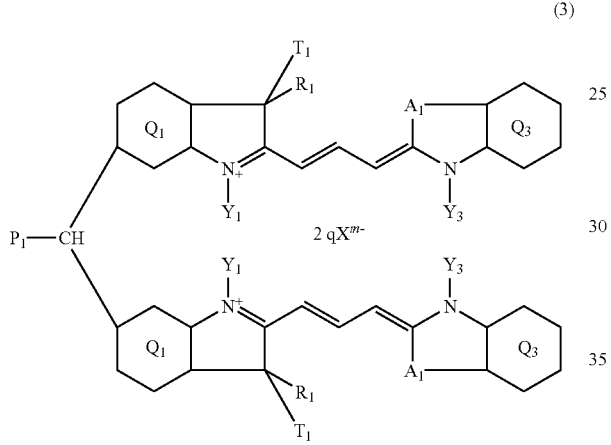

wherein each symbols are defined as above.

4) The trimethine cyanine compound according to 3), which is the compound represented by the following formula (4):

(4)

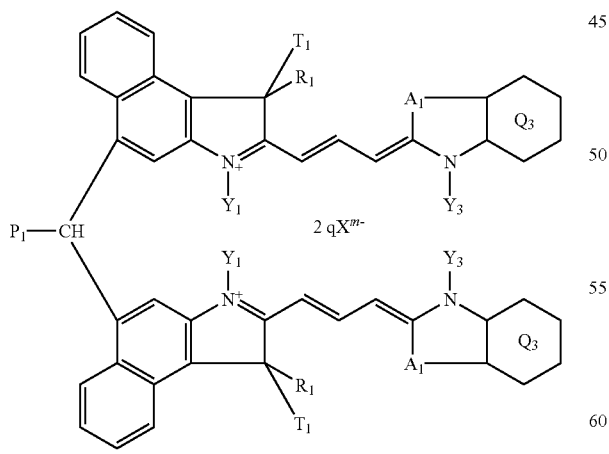

wherein each symbols are defined as above.

The trimethine cyanine compounds represented by the formulae (1), (2), (3), and (4) are novel cyanine dimmer, which is prepared by first forming indolium salt from indole, and coupling the resultant indolium salt with indolium derivative having polymethine bridge group. The preparation of the present trimethine cyanine compounds is not limited to the above process.

Accordingly, the present invention also relates to:

5) An indolium compound represented by the formula (5):

(5)

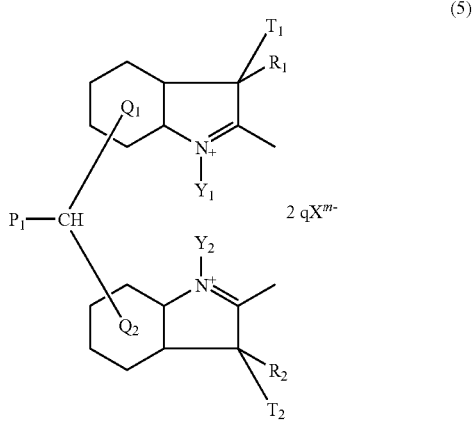

wherein each symbols are defined as above.

6) The indolium compound according to 5), which is the compound represented by the following formula (6):

(6)

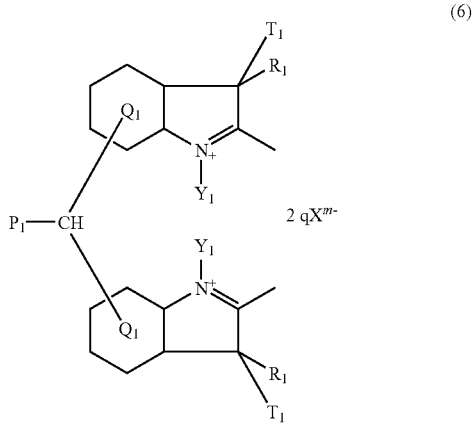

wherein each symbols are defined as above.

7) The indolium compound according to 6), which is the compound represented by the following formula (7):

(7)

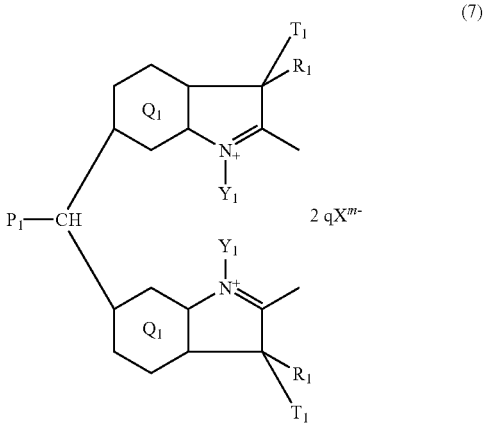

wherein each symbols are defined as above.

8) The indolium compound according to 7), which is the compound represented by the following formula (8):

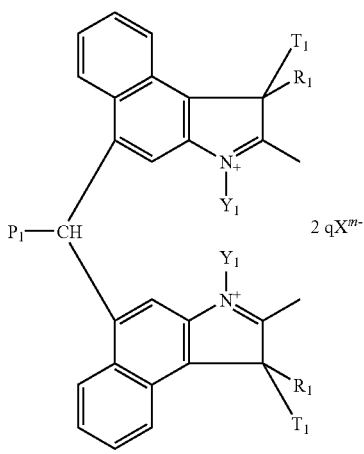

(8)

wherein each symbols are defined as above.

Accordingly, the present invention also relates to:

9) A pseudo-indolium compound represented by the formula (9):

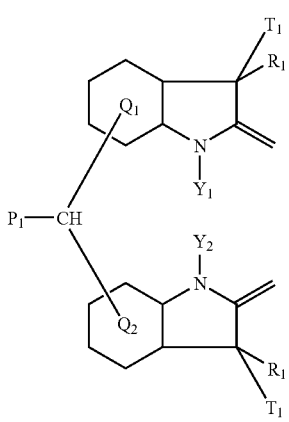

(9)

wherein each symbols are defined as above.

10) The pseudo-indolium compound according to 9), which is represented by the following formula (10):

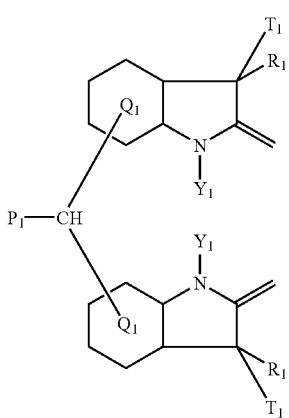

(10)

wherein each symbols are defined as above.

11) The pseudo-indolium compound according to 10), which is represented by the following formula (11):

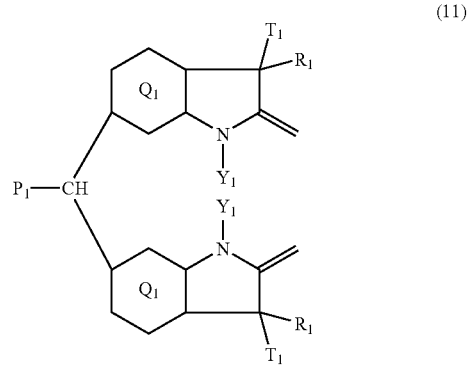

(11)

wherein each symbols are defined as above.

12) The pseudo-indolium compound according to 11), which is represented by the following formula (12):

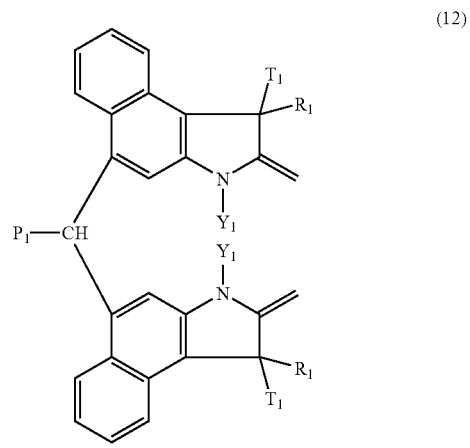

(12)

wherein each symbols are defined as above.

13) The indolium compound according to any one of 5) to 8), and The pseudo-indolium compound according to any one of 9) to 12) which is an intermediate for preparing the trimethine cyanine compound according to any one of 1) to 4).

14) An optical recording material for forming an optical recording layer, which contains the trimethine cyanine compound according to any one of 1) to 4).

15) An optical recording media, which comprises a substrate and an optical recording layer formed on the substrate, wherein the optical recording layer is a film prepared from the optical recording material according to 14).

DETAILED DESCRIPTION OF THE INVENTION

In the formulae (1), (2), (3), (4) or formulae (5), (6), (7), (8), (9), (10), (11), and (12) (hereinafter, sometimes collectively referred to formulae (1) to (12)), $P_1$ is a hydrogen atom or an organic group having 1 to 18 carbon atoms. The organic group can be optionally substituted with one or more substituents selected from the group consisting of alkyl, alkenyl, alkynyl, aryl, and arylalkyl groups. The alkyl group can be, for example, methyl, ethyl, n-propyl, isopropyl, n-butyl, isobutyl, sec-butyl, tert-butyl, n-pentyl, isopentyl, n-hexyl, cyclohexyl, etc. The alkenyl group can be, for example, ethenyl, 1-propenyl, 2-propenyl, 2-methylpropenyl, 2-butenyl, 3-butenyl, cinnamyl, etc. The alkynyl group can be, for example, ethynyl, 1-propargyl, 2-propargyl, 1-butynyl, 2-butynyl, 3-butynyl, etc. The aryl group can be, for example, phenyl, naphthyl, o-tolyl, m-tolyl, p-tolyl, 2,4-dimethylphenyl, 2,6-dimethylphenyl, 2,4,6-trimethylphenyl, o-methoxyphenyl, m-methoxyphenyl, p-methoxyphenyl, and biphenylyl, etc. The arylalkyl group can be, for example, benzyl, phenylethyl, 2-phenylethyl, 3-phenylpropyl, o-methoxybenzyl, m-methoxybenzyl, p-methoxybenzyl, etc.

In the formulae (1) to (12), $Q_1$, $Q_2$, $Q_3$, and $Q_4$ are the same or different and each represents a substituted or unsubstituted benzene ring or naphthalene ring. The substituents substituted on the phenyl or naphthyl group can include, for example, halogen atoms such as fluorine, chlorine, bromine, and iodide atoms; alkyl groups such as methyl, ethyl, propyl, isopropyl, n-butyl, isobutyl, sec-butyl, tert-butyl, n-pentyl, isopentyl, tert-pentyl, cyclopentyl, n-hexyl, cyclohexyl, heptyl, octyl group, etc.; aryl group, such as phenyl, naphthyl, 4-methylphenyl grous, etc.; alkoxyl group such as methoxy, ethoxy, n-propoxy, isopropoxy, n-butoxy, iso-butoxy groups, etc.; alkylthio group such as methylthio, ethylthio, propylthio, isopropylthio, butylthio groups, etc.; nitro group; and cyano group.

In the formulae (1) to (12), $Y_1$, $Y_2$, $Y_3$, and $Y_4$ are the same or different and each represents an organic group having 1 to 18 carbon atoms, preferably an organic group having 1 to 10 carbon atoms. The organic group includes, for example, methyl, ethyl, n-propyl, isopropyl, 2-propenyl, ethynyl, isopropenyl, n-butyl, isobutyl, tert-butyl, 2-butenyl, n-pentyl, isopentyl, neopentyl, tert-pentyl, 1-methylpentyl, 2-methylpentyl, 2-pentenyl, 2-penten-4-ynyl, n-hexyl, isohexyl, 5-methylhexyl, heptyl, and octyl, etc; benzyl, phenylethyl, 2-phenylpropyl, 3-phenylpropyl, phenyl, o-tolyl, m-tolyl, p-tolyl, 2,4-dimethylphenyl, 2,6-dimethylphenyl, 2,4,6-trimethylphenyl, o-methoxyphenyl, m-methoxyphenyl, p-methoxyphenyl, and biphenylyl.

In the formulae (1) to (12), $T_1$ and $T_2$ are the same or different and each represents a substituted or unsubstituted benzyl group, a substituted or unsubstituted allyl group, or a substituted or unsubstituted propargyl group. Examples of the substituted or unsubstituted benzyl group include benzyl, p-methylbenzyl, o-methoxybenzyl, m-methoxybenzyl, p-methoxybenzyl, and the like. Examples of the substituted or unsubstituted allyl group include allyl, 2-methylpropenyl, 2-butenyl, cinnamyl, and the like. Examples of the substituted or unsubstituted propargyl include propargyl, and 2-butynyl, and the like.

Specifically, the substituted or unsubstituted allyl group represented by $T_1$ and $T_2$ in the above formulae is represented by the following formula (13)

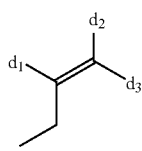

(13)

wherein $d_1$, $d_2$, and $d_3$ each represents hydrogen atom or an organic group having 1-8 carbon atoms; or $d_1$ and $d_2$, or $d_3$ and $d_4$ can combine to form a 3- to 6-member ring so that the formula (13) is represented by the following formulae (14) and (15):

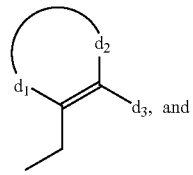

(14)

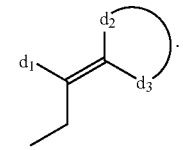

(15)

The substituted or unsubstituted propargyl group represented by $T_1$ and $T_2$ in the above formulae is represented by the following formula (16):

(16)

wherein $d_4$ represents hydrogen atom or an organic group having 1-8 carbon atoms.

The substituted or unsubstituted benzyl group represented by $T_1$ and $T_2$ in the above formulae is represented by the following formula (17)

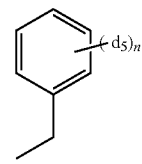

(17)

wherein $d_5$ represents hydrogen atom or an organic group having 1-8 carbon atoms; and n represents a number of 1, 2, 3, 4, or 5.

In the formulae (1) to (12), $A_1$ and $A_2$ are the same or different and each represent groups of formula

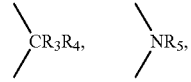

an oxygen atom, or a sulfur atom; and $R_3$, $R_4$, and $R_5$ are the same or different and each represents a hydrocarbon group having 1-18 carbon atoms. Specifically, $R_3$, $R_4$, and $R_5$ are the same or different and each represents an alkyl group having 1 to 18 carbon atoms, an alkenyl group having 2 to 18 carbon atoms, an alkynyl group having 2 to 18 carbon atoms, aryl group, aralkyl group, a monocyclic hydrocarbyl group, or a polycyclic hydrocarbyl group, all of which are substituted or unsubstituted; or $R_3$ and $R_4$ combines together to form a 3- to 6-member carbon cyclic group, which is further optionally fused with a benzene ring. Examples of the alkyl group include methyl, ethyl, n-propyl, isopropyl, n-butyl, isobutyl, sec-butyl, tert-butyl, n-pentyl, isopentyl, tert-pentyl, cyclopentyl, n-hexyl, cyclohexyl, heptyl, and octyl, etc. Examples of the alkenyl group include 1-propenyl, 2-propenyl, 2-methylpropenyl, 2-butenyl, 3-butenyl, cinnamyl, etc. Examples of the alkynyl group include 1-propargyl, 2-propargyl, 2-butynyl, 3-butynyl, etc. Examples of the aryl group include phenyl, naphthyl, o-tolyl, m-tolyl, p-tolyl, 2,4-dimethylphenyl, 2,6-dimethylphenyl, 2,4,6-trimethylphenyl, and biphenylyl, etc. Examples of the aralkyl group include benzyl, phenylethyl, 3-phenylpropyl, o-methoxybenzyl, m-methoxybenzyl, p-methoxybenzyl, etc. Those groups can be further substituted with one or more substitutents selected from the group consisting of: alkoxyl group such as methoxy, trifluoromethoxy, ethoxy, n-propoxy, isopropoxy, butoxy, tert-butoxy, and pentoxy; aryloxy group such as phenoxy; aralkyloxy group such as benzyloxy; alkoxycarbonyl group such as methoxycarbonyl, trifluoromethoxycarbonyl, ethoxycarbonyl, propoxycarbonyl; alkanoyloxy group such as acetyloxy, trifluoroacetyloxy; halogen group such as fluorine, chlorine, bromine, and iodine; amido group, carboxy group, keton group, aldehyde group, nitrile group, nitro group, sulfone group, sulfoxide group; and heterocyclic group such as furyl, pyrrolyl, thienyl, pyridyl, and indolyl groups.

In the formulae (1) to (12), $R_1$ and $R_2$ are defined as the same as $R_3$, $R_4$, and $R_5$.

In the formulae (1) to (12), $X^{m-}$ represents a counterion having m valence. The counterion is selected depending on the final use and the physical properties of the trimethine cyanine compound, such as solubility in solvent (such as 2,2,3,3-tetrafluoro-1-propanol (TFP)), heat-resistance, stability, and explosion, etc. Examples of the counterion include halide such as iodide, bromide, chloride, and fluoride; inorganic acid ion such as phosphate ion, perchlorate ion, periodate ion, hexafluorophosphate ion, hexafluoroantimonate ion, hexafluorostannate ion, and tetrafluoroborate ion; organic acid ion such as thiocyanate ion, benzenesulfonate ion, naphthylsulfonate ion, p-tolylsulfonate ion, ethylsulfonate ion, benzoate ion, trifluoroacetate ion, trichloroacetate, methanesulfonate ion, trifluoromethanesulfonate ion; and organic metal coordinating anion such as azo metal coordinating anion, bisphenyldithiol, thiocatechol chealate, thiobisphenorate chealate.

Among them, the preferable one is the coordinating counterion containing fluoroine and element of Group 5A in the Element Table such as phosphine, antimony, and bismuth, for examples, hexafluorophosphate ion and hexafluoroantimonate ion; and azo metal coordinating anion. By carrying the counterion, the trimethine cyanine compound exhibits relative high heat-resistance, easily operation, and good solubility in solvent such as TFP.

Moreover, the above organic metal coordinating anion generally exhibits excellent ability of quenching singlet oxygen and thus exhibits excellent light-resistance and weather-resistance when using as a recording layer in an optical recording medium. Among the above organic metal coordinating anion, the azo metal coordinating anion and bisphenyldithiol chealate are commonly used and mentioned in, for example, Taiwan Patent Publication Nos. 434245, 493171, 572969, and USPs 4713314, 526478, and Japanese Patent Laid-open Publication No. JP6-239028. Examples of the azo metal coordinating anion and biphenyldithiol chelate are represented by the following formulae (18), (19), and (20), respectively:

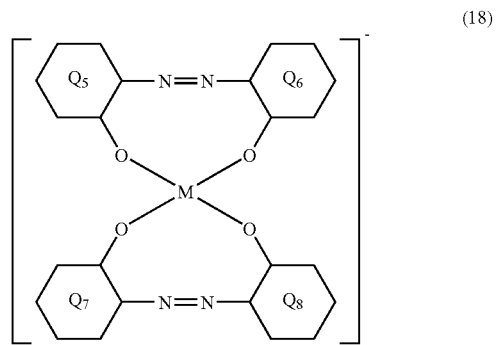
(18)

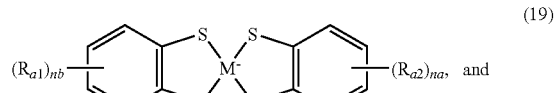
(19)

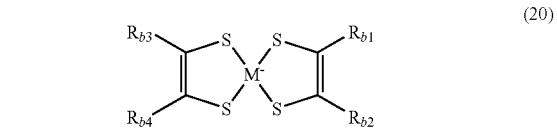
(20)

wherein $Q_5$, $Q_6$, $Q_7$, and $Q_8$ are the same and different and each represents a substituted or unsubstituted aryl group (such as benzene ring) or heteroaryl group; $R_{a1}$, $R_{a2}$, $R_{b1}$, $R_{b2}$, $R_{b3}$, and $R_{b4}$ each represents an alkyl group, an aralkyl group, or an aryl group; na and nb each represents 0, 1, 2, 3, or 4.

The trimethine cyanine compound according to the present invention is, for example, the following compounds, but not limited thereto.

Compound No. 1

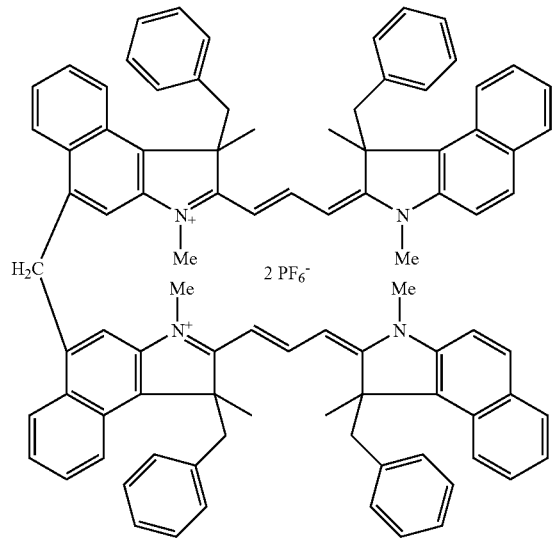

Compound No. 2

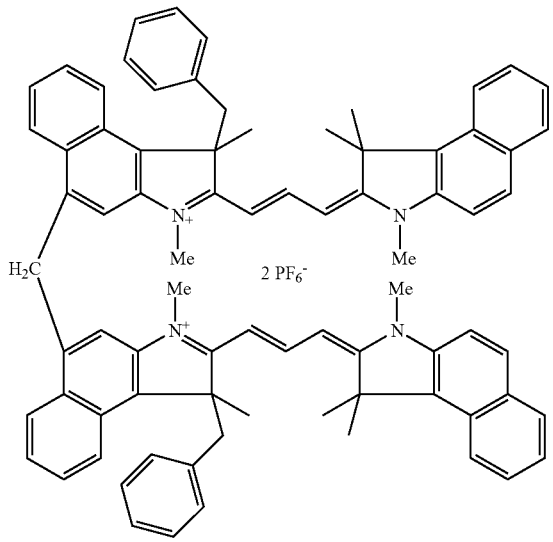

-continued
Compound No. 3
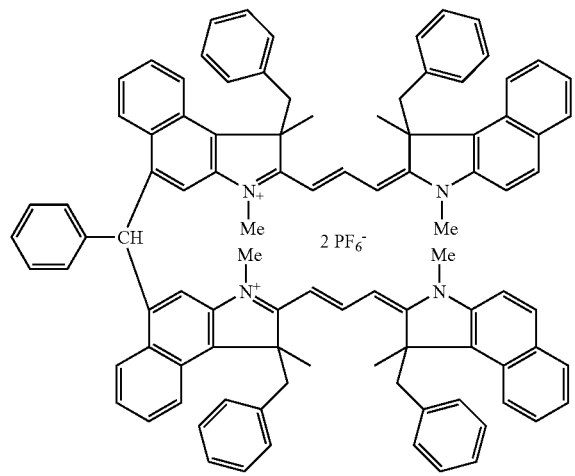
Compound No. 4
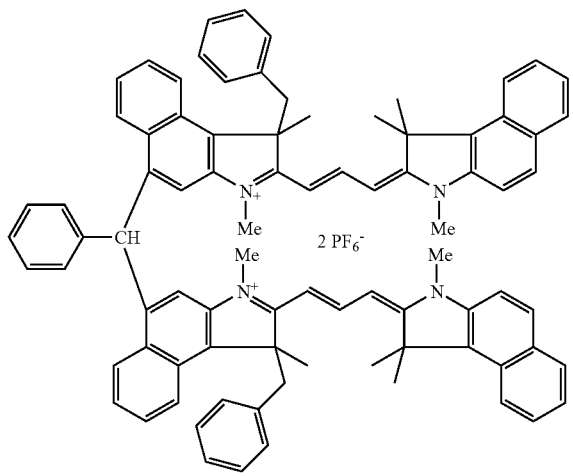
Compound No. 5
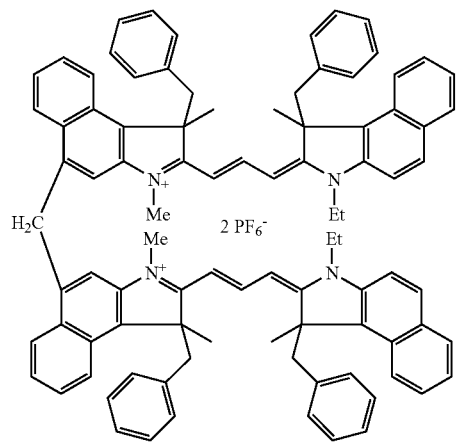
Compound No. 6
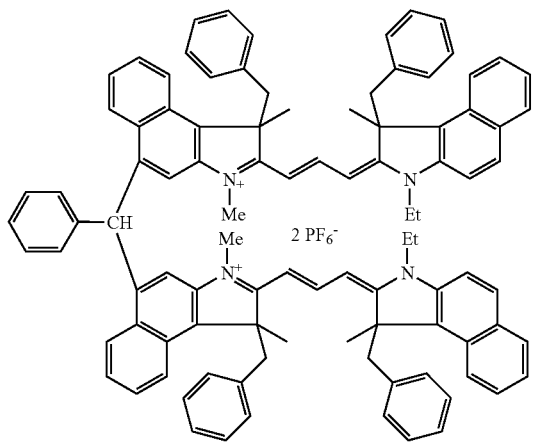
Compound No. 7
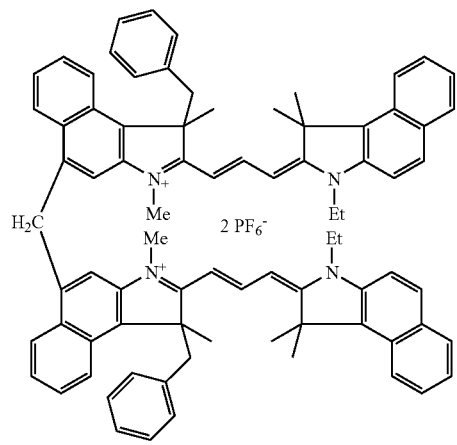
Compound No. 8
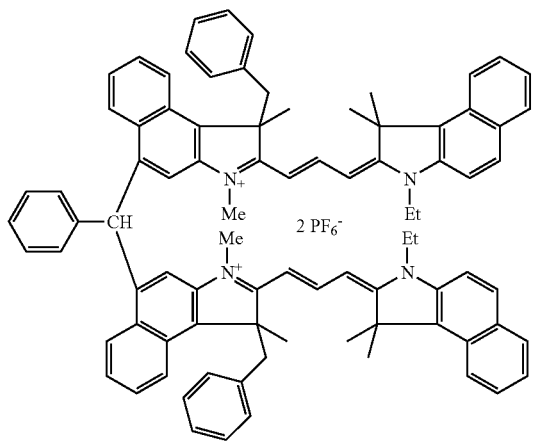

-continued
Compound No. 9
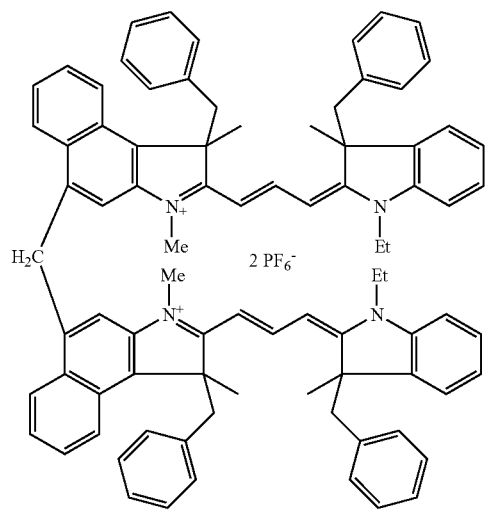
Compound No. 10
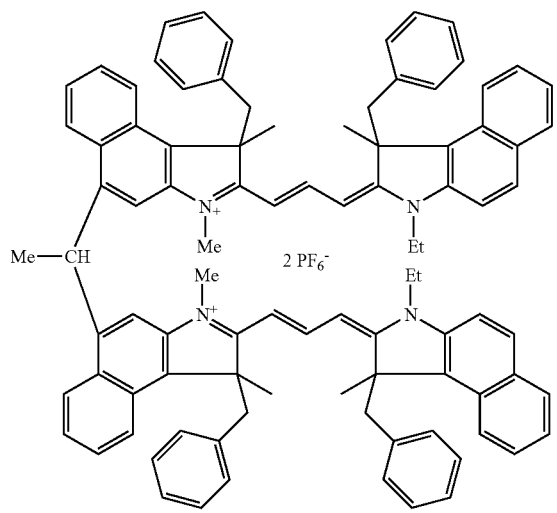
Compound No. 11
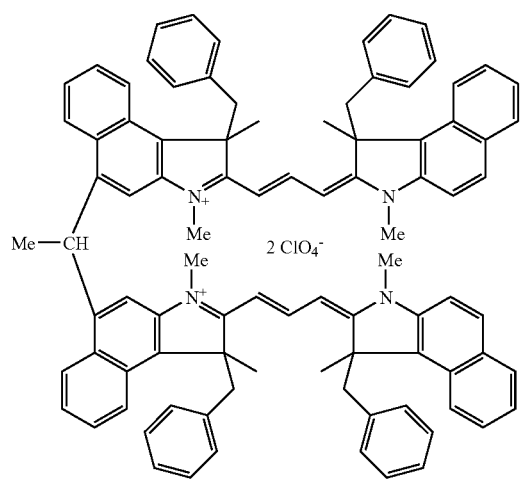
Compound No. 12
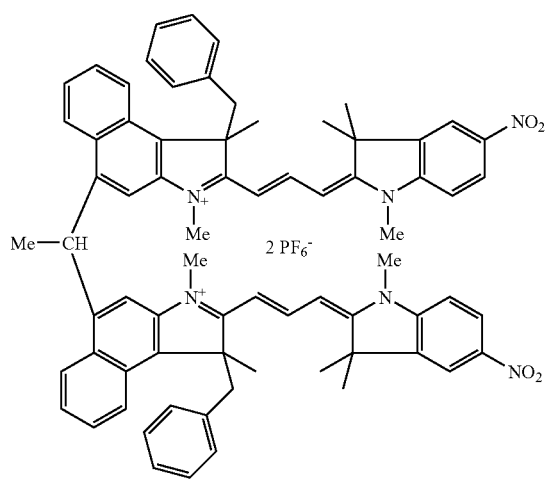
Compound No. 13
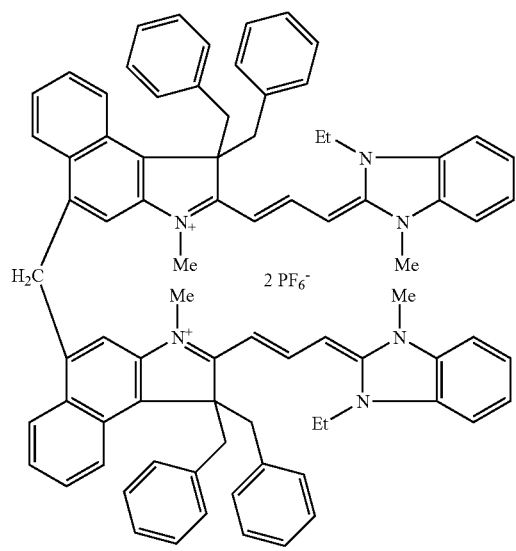
Compound No. 14
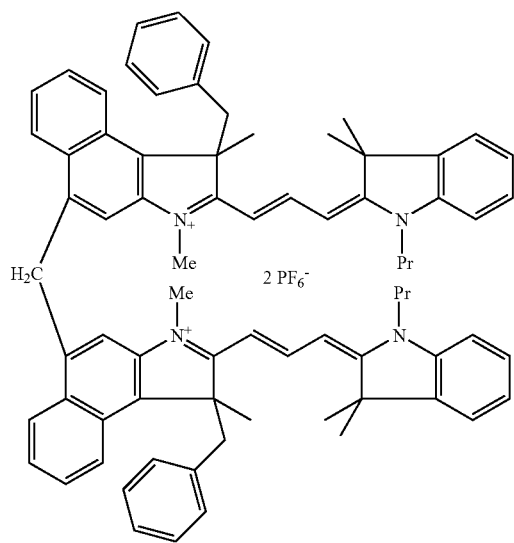

-continued
Compound No. 15
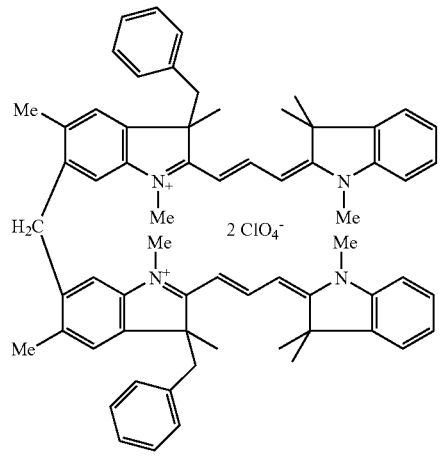
Compound No. 16
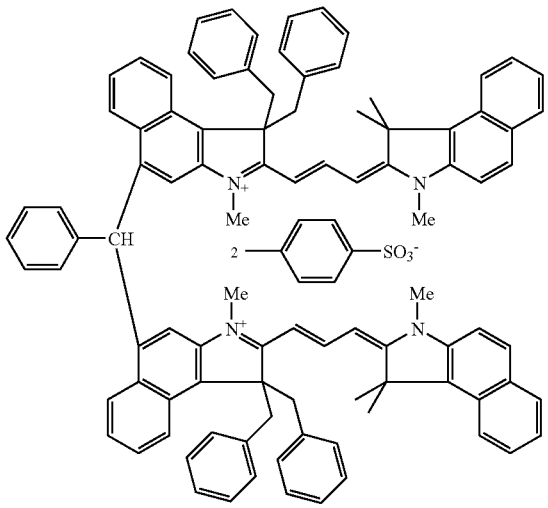
Compound No. 17
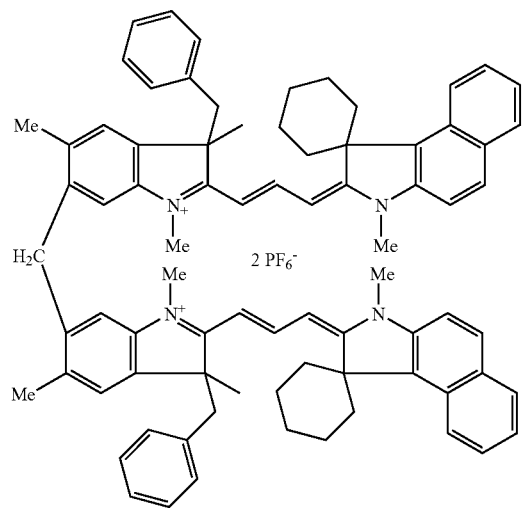
Compound No. 18
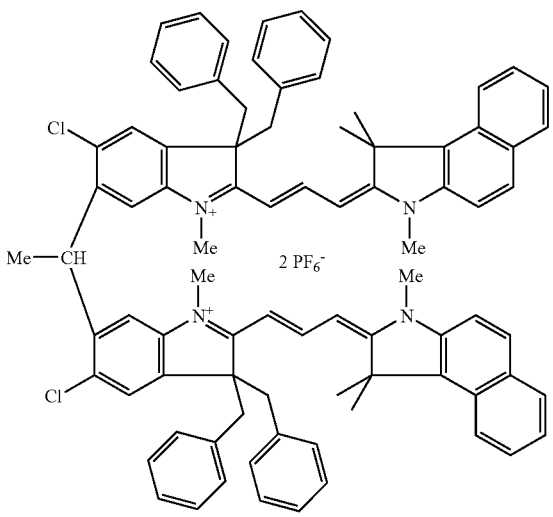
Compound No. 19
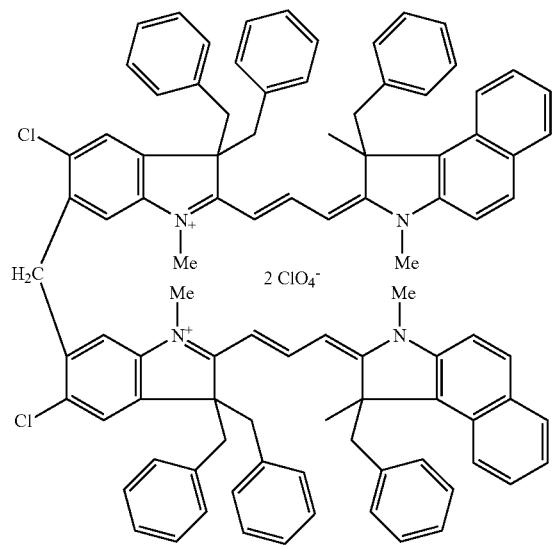
Compound No. 20
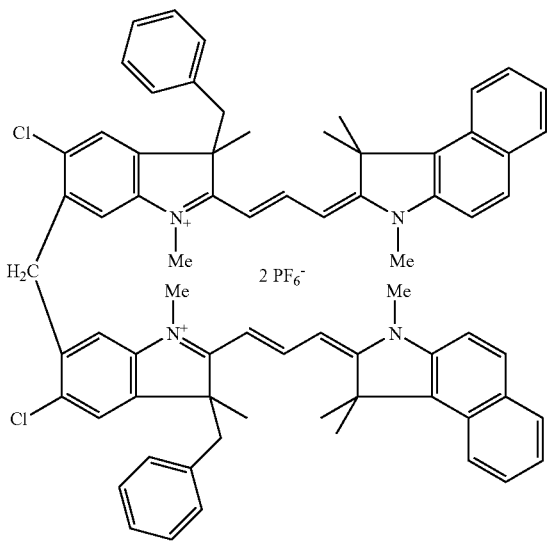

-continued
Compound No. 21
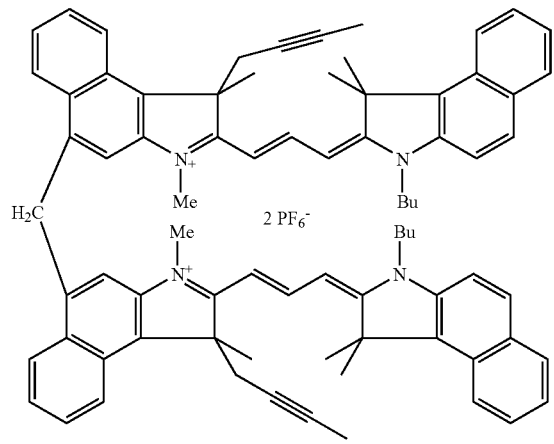
Compound No. 22
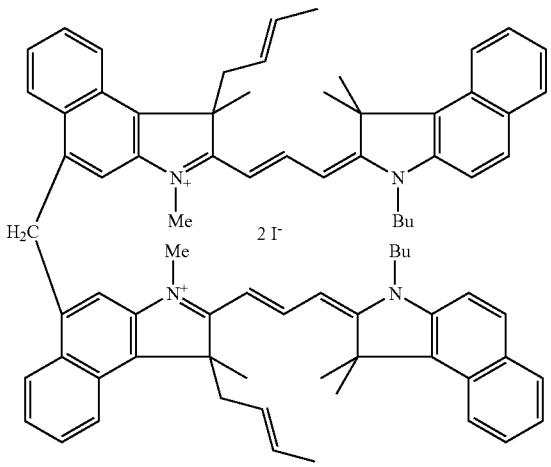
Compound No. 23
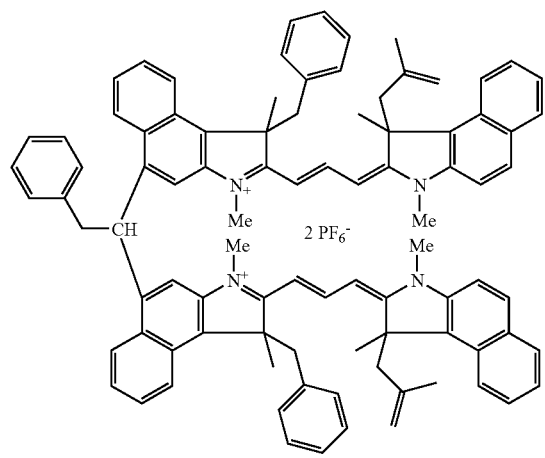
Compound No. 24
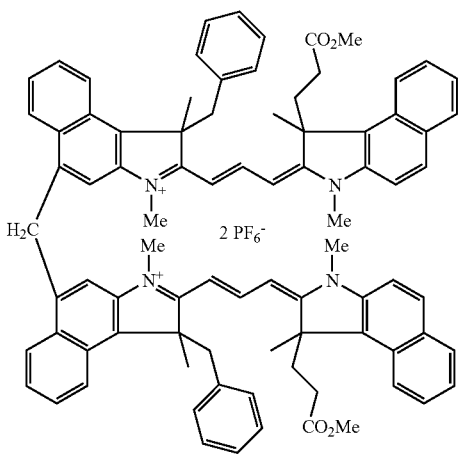
Compound No. 25
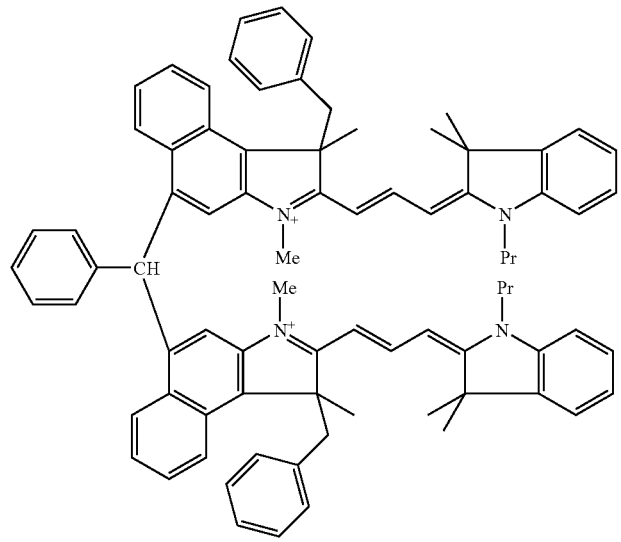
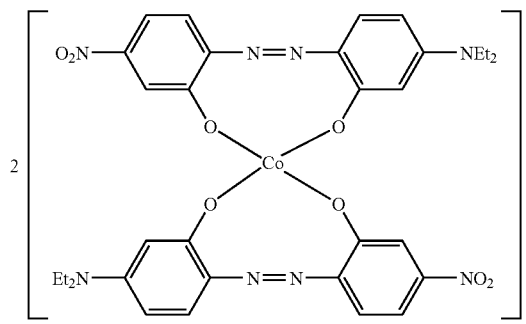

-continued
Compound No. 26
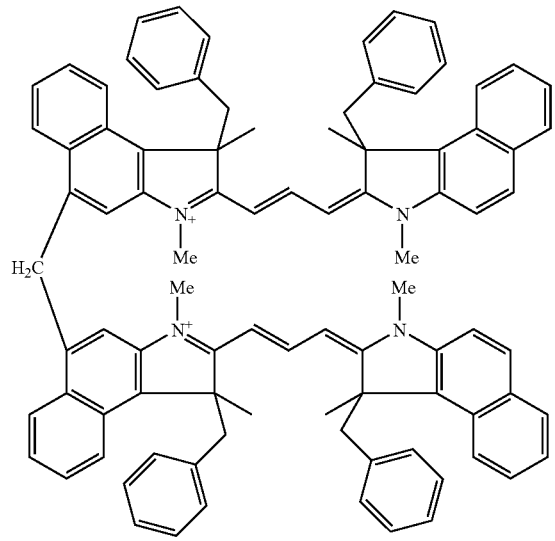
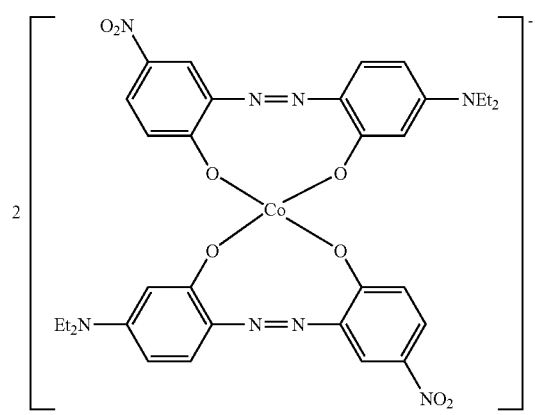
Compound No. 27
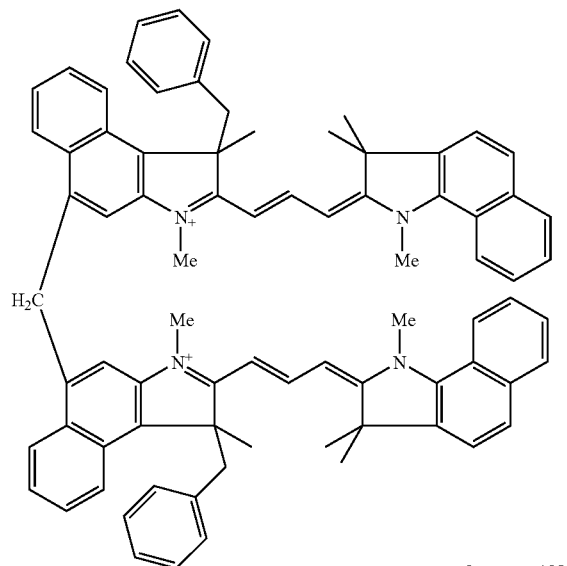
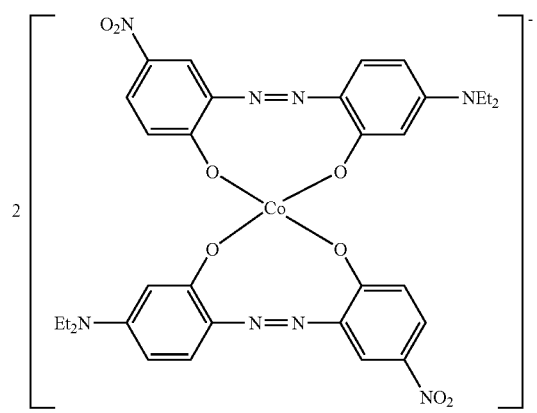
Compound No. 28
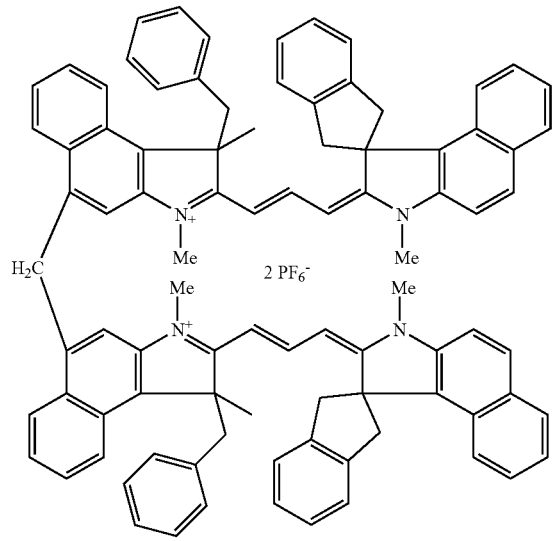
Compound No. 29
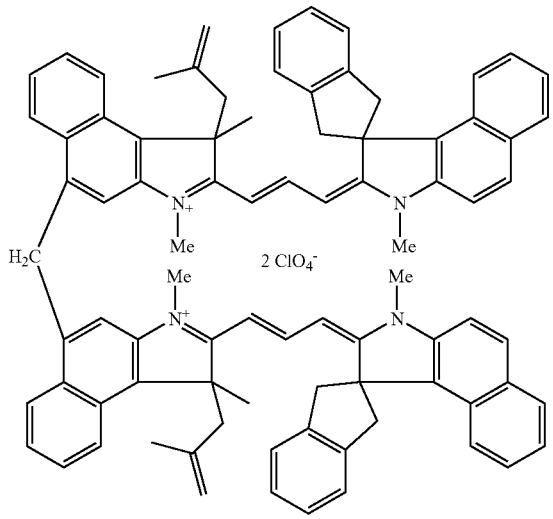

-continued
Compound No. 30
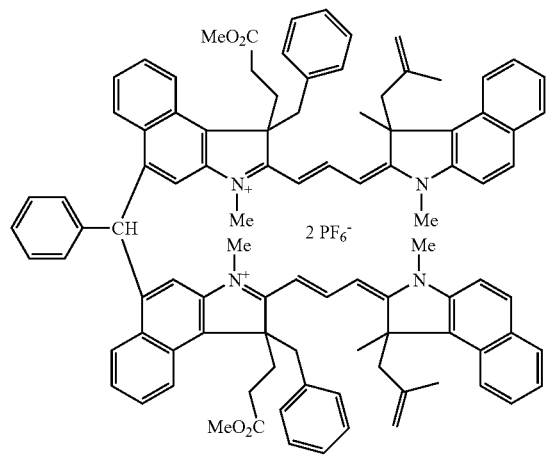
Compound No. 31
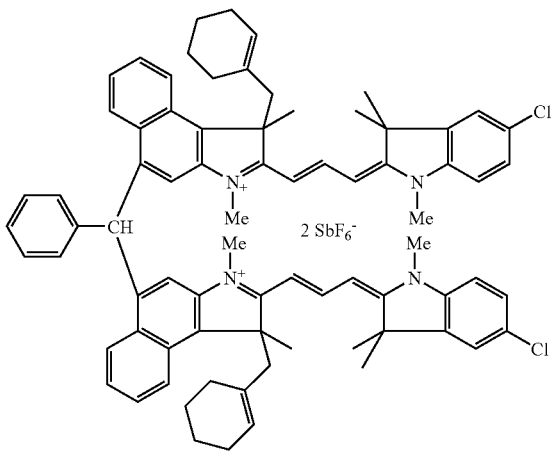
Compound No. 32
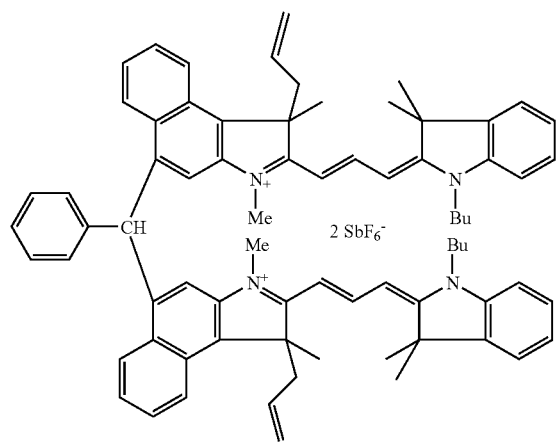
Compound No. 33
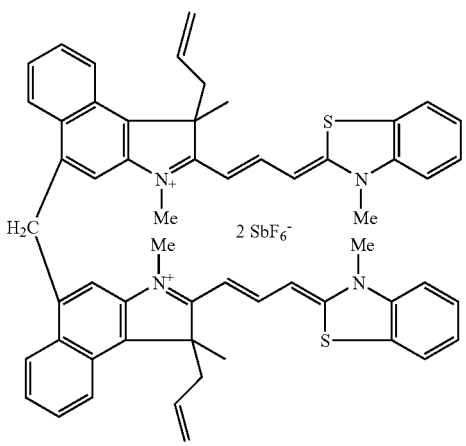
Compound No. 34
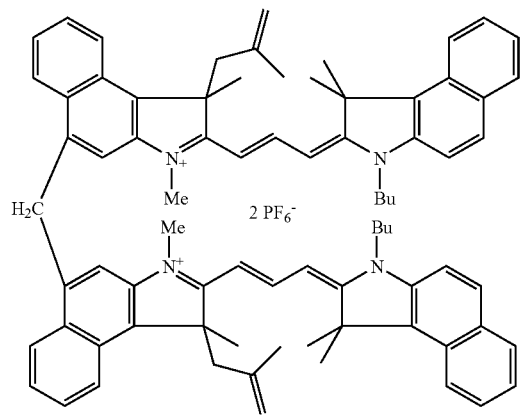
Compound No. 35
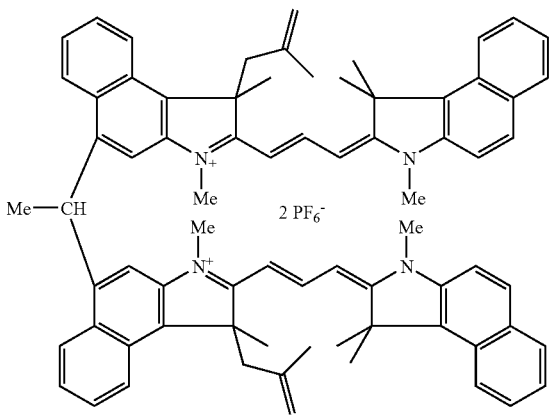

Compound No. 36

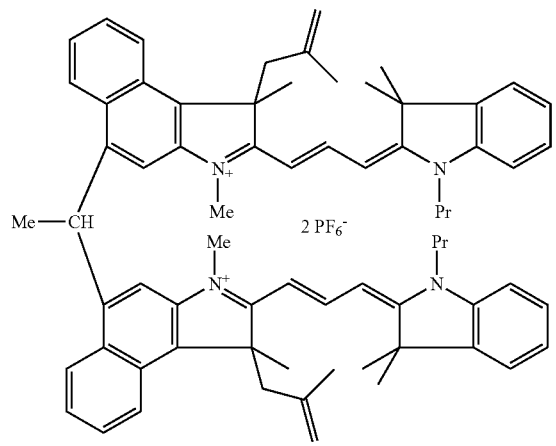

Compound No. 37

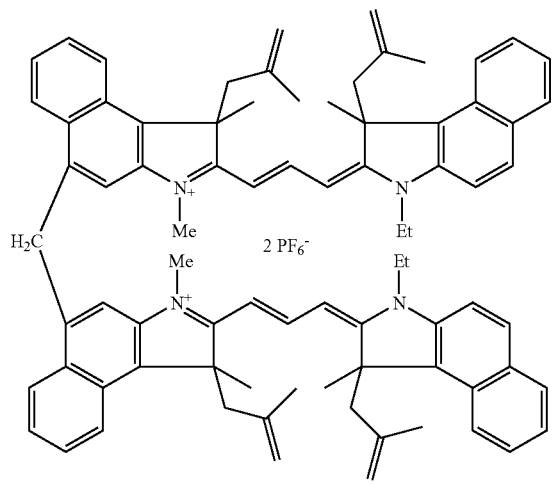

The trimethine cyanine compound of the present invention is prepared by first forming an indolium compound (6), and coupling the indolium compound (6), N,N'-diphenylformidine (22) and indolium derivative (21) to form trimethine cyanine compound of formula (2) as mentioned below. But in the present invention, its preparation is not limited thereto.

preferably from 0° C. to 100° C. The reaction pressure can be in a range of from 0.5 Bar to 30 Bar, preferably from 1 Bar to 10 Bar. Examples of the compound (24) include, for example, allyl halide compound, benzyl halide compounds or propargyl halide compounds. Examples of the Louis acids (LA) compound (25) include, for example, zinc chloride, zinc bromide, zinc iodide, aluminum trichloride, etc.

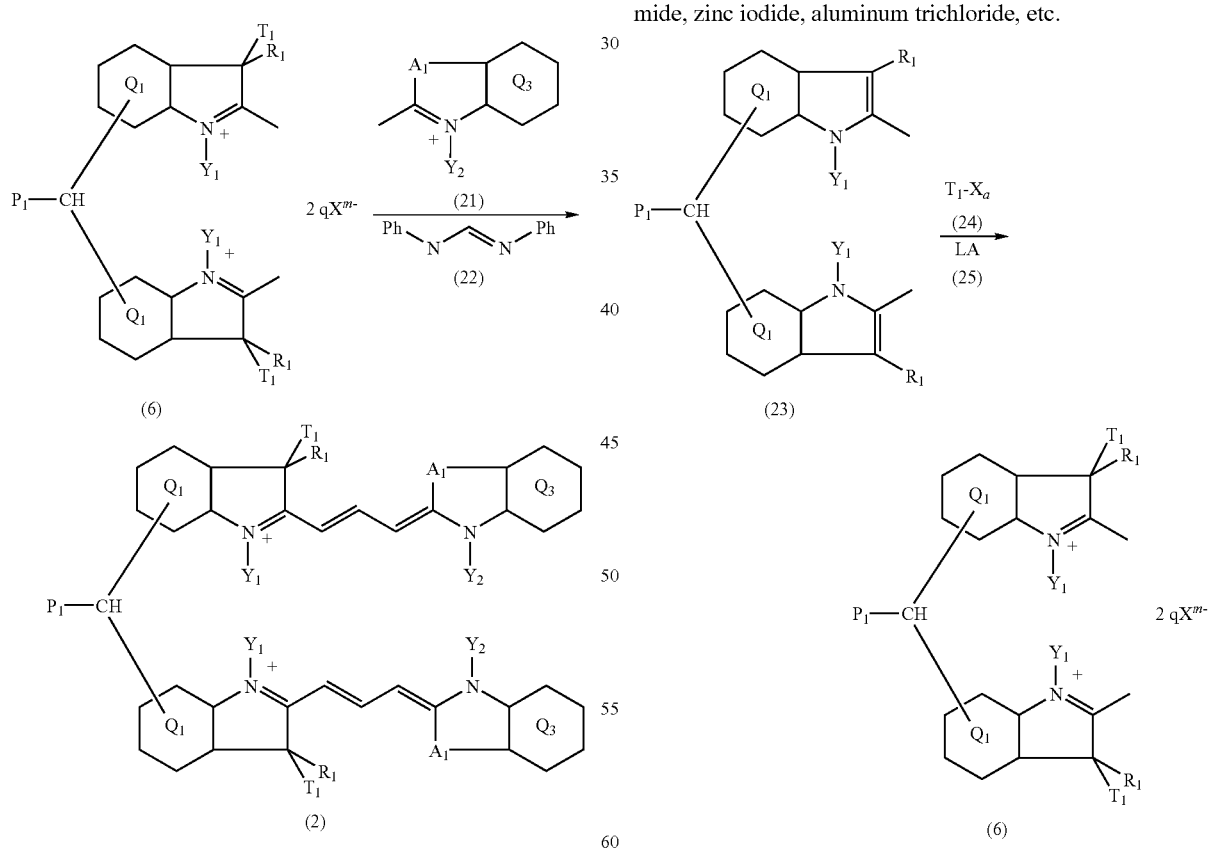

wherein each symbols are defined as above.

The indolium compound (6) is prepared, for example, by reacting indole compound (23) and a compound of formula $T_1$-$X_a$ (24) (wherein $T_1$ is defined as above and $X_a$ is halogen atom or a leaving group) in the absence or presence of Louis acids (LA) compound (25), as shown in below. The reaction temperature can be in a range of from −30° C. to 180° C., wherein each symbols are defined as above.

Representative examples of allyl halide compounds include allyl chloride, allyl bromide, 1-chloro-2-methyl-2-propylene, 1-bromo-2-methyl-propylene, 1-chloro-2-butene, cinnamyl chloride, cinnamyl bromide, etc. Representative examples of benzyl halide compounds include benzyl chloride, benzyl bromide, p-methylbenzyl chloride, p-methoxybenzyl chloride, etc. Representative examples of propargyl halide compounds include propargyl chloride, 1-bromo-2-bytyne, 3-chloro-1-phenyl propyne, etc. However, the above listed compounds are only for illustration but not limited thereto.

The indole (23) can be prepared by catalytic reacting an indole compound (26) and a saturated or unsaturated aldehyde compound (27) in the presence of acidic compound (HA)(28), as shown below. The aldehyde compound (27) includes aliphatic aldehyde, aromatic aldehyde, acetal, hemiacetal, vinyl ether, and polyaldehydes. Examples of the saturated aliphatic aldehyde compound include, for example, formaldehyde, acetaldehyde, propionaldehyde, n-butyraldehyde, iso-butyraldehyde, n-valeraldehyde, 2-methylbutyraldehyde, etc. Examples of the unsaturated aliphatic aldehyde compound include, for example, acrolein, 2-methacrolein, crotonaldehyde, etc. Examples of the aromatic aldehyde compound include, for example, benzaldehyde, p-methylbenzaldehyde, o-methylbenzaldehyde, m-methylbenzaldehyde, anisaldehyde, etc. Examples of the acetal compound include, for example, dimethoxymethane, diethoxymethane, 1,1-dimethoxyethane, 1,1-diethoxyethane, 1,1-dimethoxypropane, 1,1-diethoxypropane, 1,1-dimethoxybutane, 1,1-diethoxybutane, or acrolein dimethyl acetal, acrolein diethyl acetal, methacrolein dimethyl acetal, benzaldehyde dimethyl acetal, benzaldehyde diethyl acetal, anisaldehyde dimethyl acetal, or anisaldehyde diethyl acetal, etc. Examples of the vinyl ether include, for example, methyl vinyl ether, ethyl vinyl ether, propyl vinyl ether, butyl vinyl ether, etc. Examples of the polyaldehydes include, for example, paraformaldehyde, 1,3,5-trioxane, 2,4,6-trimethyl-1,3,5-trioxane, 2,4,6-tri-isopropyl-1,3,5-trioxane, etc. The acidic compound (HA)(28) can be organic acid and inorganic acid. Examples of the organic acid include, for example, alkylsulfonate, benzene sulfonate, carboxylic acids, such as, methanesulfonic acid, p-toluenesulfonic acid, benzenesulfonic acid, trifluorormethanesulfonic acid, difluoromethanesulfonic acid, monochloromethanesulfonic acid, trifluoroacetic acid. Examples of the inorganic acid include, for example, hydrochloric acid, hydrobromic acid, hydroiodic acid, sulfuric acid, phosphoric acid, phosphorous acid. Among them, p-toluenesulfonic acid, methanesulfonic acid and sulfuric acid are preferable.

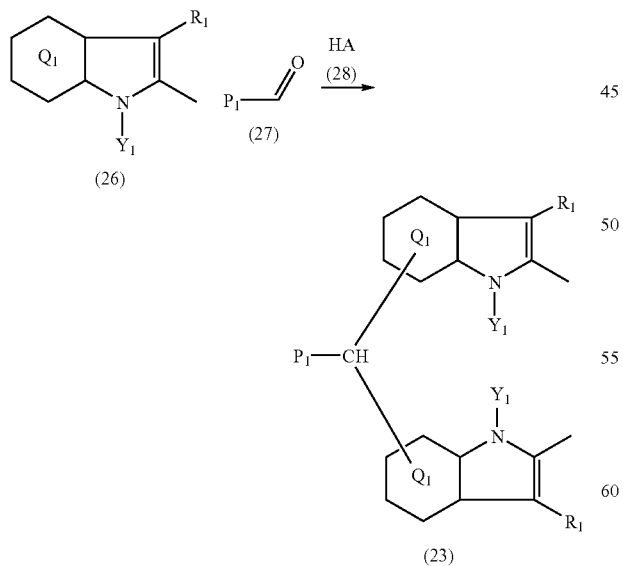

wherein each symbols are defined as above.

The present invention is illustrated by reference to the following Examples which are used only for illustrating the invention but not limit the scope of the present invention.

EXAMPLE 1

Preparation of Compound No. 1

(1) Preparation of Indole Compound 38

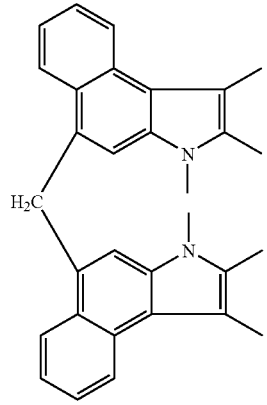

Into a 500-ml flask equipped with a stirrer was added with 168 ml of 1,2-dichloroethane, 41.8 g of 1,2,3-trimethylbenzo[e]indole, and 3.6 g of 1,3,5-trioxane and the mixture was stirred. Then the mixture was added with 11.4 g p-toluenesulfonic acid while heating and reacting at 60° C. for 20 hour. After completing the reaction, the mixture was added with 120 mL of 1,2-dichloroethane and cooled to 30° C. and was added with 50 ml water. The result crystal was filtered and washed with water then with 1,2-dichloroethane and then with methanol to obtain 16.7 g (38% in yield) indole compound 38 in grey powdery solid after drying.

Melt point (DSC-TGA, 10° C./min ramp under nitrogen): 278.4° C.

$^1$H-NMR (DMSO-$d_6$):

δ8.47 (d, J=8.0 Hz, 2H), 8.07 (d, J=8.0 Hz, 2H), 7.51 (t, J=8.0 Hz, 2H), 7.31 (t, J=8.0 Hz, 2H), 7.27 (s, 2H), 4.93 (s, 2H), 3.50 (s, 6H), 2.58 (s, 6H), 2.35 (s, 6H)

(2) Preparation of Pseudo-Indolium Compound 39

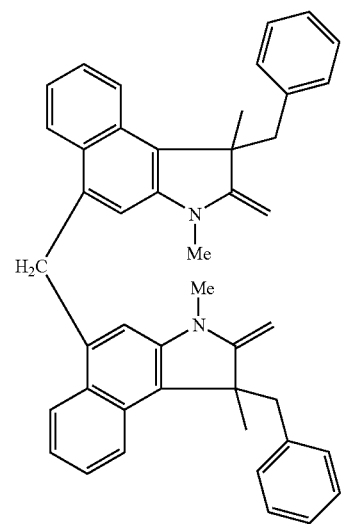

Into a 500-ml flask equipped with a stirrer and a nitrogen blanket was added with 45 ml of acetonitrile and 31.7 g (0.25 mol) of benzyl chloride, and then added with 21.5 g (0.05=1) of the indole compound 38 prepared in the above (1) while stirring thoroughly. The resultant mixture was then added with 17.7 g (0.13 mol) of zinc chloride and heated at 60° C. for 5 hours.

After completing the reaction, the mixture was cooled to 30° C. and was added with 60 ml of ethyl acetate and 120 g of 10% ammonia water and then its temperature was increased to 55° C. and stirred for 1 hour. The mixture was cooled and the solid was filtered and than stirred with 40 ml of water and 40 ml of ethyl acetate for 20 min. The solid was filtered and washed with water and then ethyl acetate to obtain 23.49 g (77% in yield) pseudo-indolium compound 39 in crystal after drying. $^1$H-NMR (CDCl$_3$):

δ8.10 (d, J=8.4 Hz, 2H), 7.86 (d, J=8.4 Hz, 2H), 7.45 (m, 2H), 7.17 (m, 2H), 6.91 (s, 2H), 6.87 (m, 4H), 6.71 (m, 4H), 6.30 (s, 2H), 4.70 (m, 2H), 3.97 (s, 2H), 3.93 (s, 2H), 3.63 (m, 2H), 2.94 (m, 2H), 2.62 (s, 3H), 2.60 (s, 3H), 1.80 (s, 6H) [2 stereoisomers with integrate ratio ~1:1].

(3) Preparation of Compound No. 1

Compound No. 1

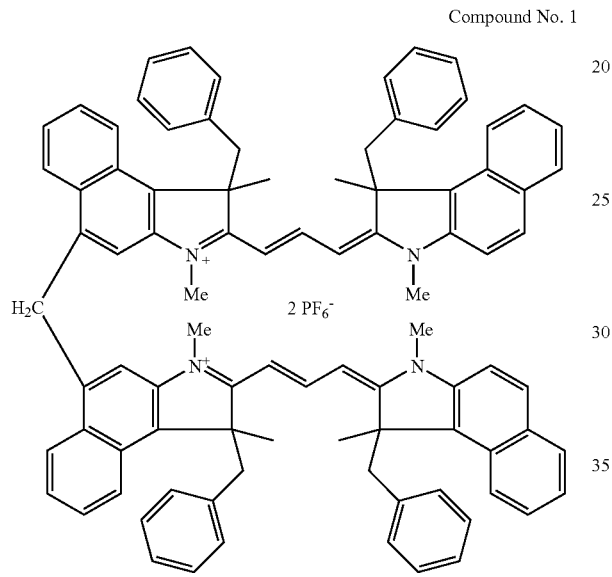

Into a flask was added with 0.02 mol of indole derivative 40 as shown below, 15 ml of acetonitrile and 0.8 ml of acetic anhydride and stirred thoroughly. 0.01 mol of the pseudo-indolium compound 39 prepared in above (2) and 2.2 g of triethylamine were added. The mixture was stirred at 78° C. for 4 hours to obtain a dye solution. Into another flask was added with 75 ml of methanol and 8 ml of water and cooled to 5° C. in an ice-water bath. Then the dye solution was added dropwise into the cooled methanol to crystallize. The crystal was filtered to obtain titled compound (Compound No. 1) in brown crystal, which was dried to obtain 11.2 g (73% in yield)

Indole Derivative 40:

40

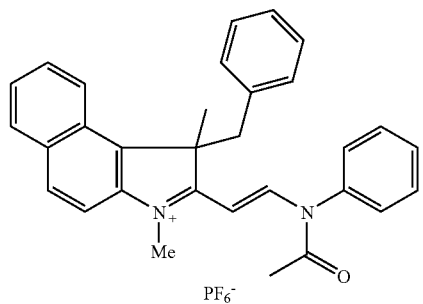

Property of the Compound No. 1

Optical property (in dichloromethane, 0.5×10$^{-5}$ g/ml): λmax 615 nm

Melt point (DSC-TGA, 10° C./min ramp under nitrogen): 214.5° C.

EXAMPLE 2

Preparation of Compound No. 5

(1) Preparation of Indolium Compound 41

41

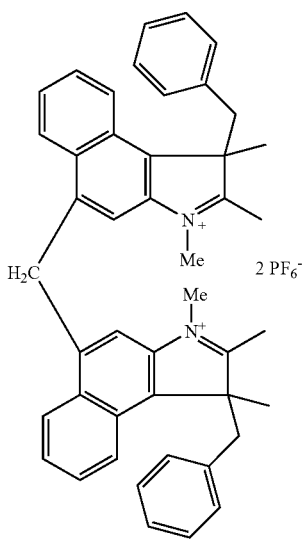

Into a 500-ml flask equipped with a stirrer and a nitrogen blanket was added with 50 ml of acetonitrile and 31.7 g (0.25 mol) of benzyl chloride, and then added with 0.05 mol of the indole compound 38 prepared in the above Example 1(1) while stirring thoroughly. The resultant mixture was then added with 17.7 g of zinc chloride and heated at 71° C. for 3 hours.

After completing the reaction, the mixture was cooled to 30° C. and was added with 100 ml of xylene and 110 g of 10% sodium hydroxide and then its temperature was increased to 55° C. and stirred for 1 hour. The mixture was cooled and the solid was filtered and washed with water then ethyl acetate. The washing and the filtrate were combined and the mixture was separated into an aqueous layer and an organic layer. The aqueous layer was discarded and the organic layer was put into a flask. The flask was cooled to 20° C. and added with 35 g of acetic acid and then added with a mixture of 18.4 g of KPF$_6$ and 50 ml H$_2$O and stirred for 1 hour. The resultant crystal was filtered and washed with water then toluene to obtain 39.05 g (86.5% in yield) indolium compound 41 in crystal after drying.

Melt point (DSC-TGA, 10° C./min ramp under nitrogen): 225.3° C. (decomposition)

(2) Preparation of Compound No. 5

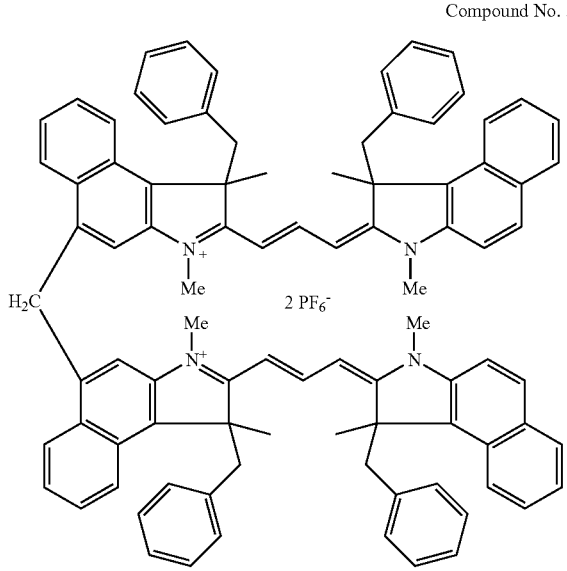

Compound No. 5

Into a 250 ml flask was added with 0.04 mol of indole derivative 42 as shown below, 50 ml of acetonitrile and 1.2 ml of acetic anhydride and stirred thoroughly. 0.02 mol of the indolium compound 41 prepared in Example 2(1) and 4.5 g of triethylamine were added. The mixture was stirred at 75° C. for 1 hour to obtain a reaction solution. Into another flask was added with 200 ml of methanol and cooled to 5° C. in an ice-water bath and then added dropwise with the reaction solution to crystallize. The crystal was filtered and added with 75 ml of dimethyl formamide and heated at 60° C. to obtain a dye solution. Into another flask was added with 330 ml of methanol and cooled to 5° C. in an ice-water bath. Then the dye solution was added dropwise into the cooled methanol to crystallize. The crystal was filtered to obtain titled compound (Compound No. 5) in brown crystal, which was dried to obtain 28.59 g (92% in yield).

Indole Derivative 42

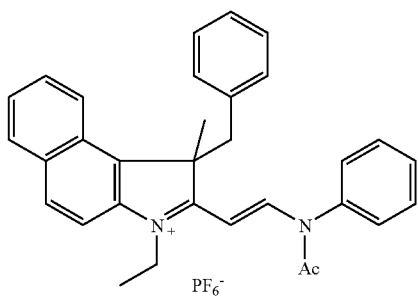

42

Property of the Compound No. 5

Optical property (in dichloromethane, $0.5 \times 10^{-5}$ g/ml): λmax 614 nm

Melt point (DSC-TGA, 10° C./min ramp under nitrogen): 212.7° C. (decomposition)

EXAMPLE 3

Preparation of Compound No. 7

Preparation of Compound No. 7

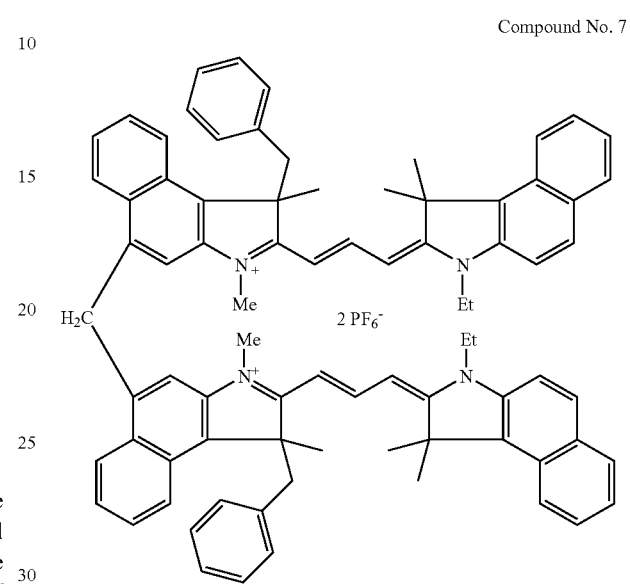

Compound No. 7

Into a 250 ml flask was added with 0.0492 mol of indole derivative 43 as shown blow, 35 ml of acetonitrile and 0.8 ml of acetic anhydride and stirred thoroughly. 0.0246 mol of the pseudo-indolium compound 39 prepared in Example 1(2) and 0.75 g of triethylamine were added. The mixture was stirred at 75° C. for 1 hour and then cooled to 65° C. 100 ml of methanol was added to crystallize and cooled to 30° C. The crystal was filtered to obtain titled compound (Compound No. 7) in brown crystal, which was dried to obtain 28.36 g (82.5% in yield).

Indole Derivative 43

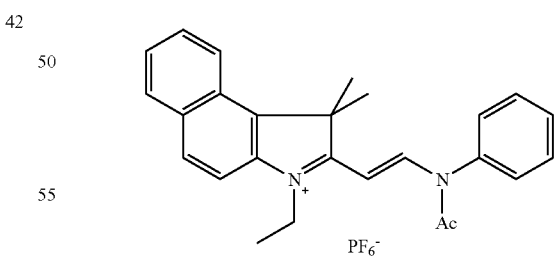

43

Property of the Compound No. 7

Optical property (in dichloromethane, $0.5 \times 10^{-5}$ g/ml): λmax 608 nm

Melt point (DSC-TGA, 10° C./min ramp under nitrogen): 224.1° C. (decomposition)

EXAMPLE 4

Preparation of Compound No. 14

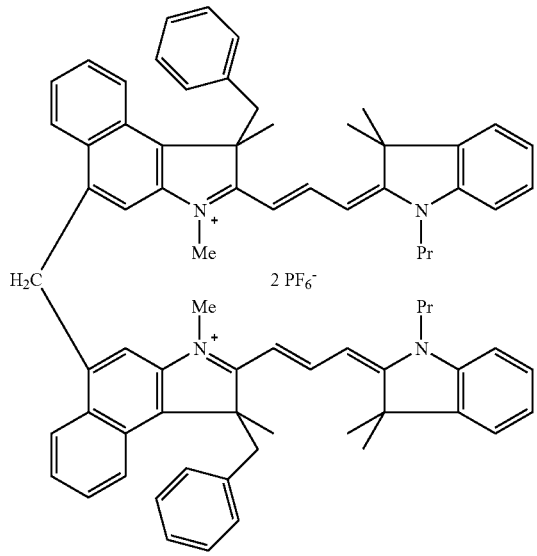

Compound No. 14

Into a flask was added with 0.01 mol of indole derivative 44 as shown blow, 10 ml of acetonitrile and 1.2 ml of acetic anhydride and stirred thoroughly. 0.02 mol of the indolium compound 41 prepared in Example 2(1) and 1.1 g of triethylamine were added. The mixture was stirred at 90° C. for 3 hours and to obtain a reaction solution. Into another flask was added with 50 ml of methanol and cooled to 5° C. in an ice-water bath and then added dropwise with the reaction solution to crystallize. The crystal was filtered to obtain titled compound (Compound No. 14) in brown crystal, which was dried to obtain 5.46 g (82% in yield).

Indole Derivative 44

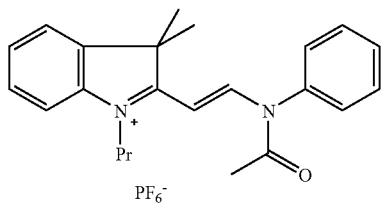

Property of the Compound No. 14

Optical property (in dichloromethane, $0.5 \times 10^{-5}$ g/ml): λmax 588 nm

Melt point (DSC-TGA, 10° C./min ramp under nitrogen): 213.9° C. (decomposition)

Experimental Example 1

0.3 g of Compound No. 1 and 0.7 g of Compound No. 14 were added into 90 g of 1,1,2,2-tetrafluoropropanol and stirred at room temperature for 4 hours to form a homogeneous solution (weight ratio of Compound No. 1 to Compound No. 14 was 30:70). The solution was filtered by Teflon filter membrane having a pore size of 100 nm. The resultant filtrate was spin-coated on a circular transparent polycarbonate substrate having a diameter of 120 mm and a thickness of 0.6 mm first at 450 rpm for 5 seconds and then at 4500 rpm for 10 seconds. The substrate was formed with a spiral trench wherein the trench depth was 160 nm, half height width was 340 nm, a distance between two adjacent trenches was 740 nm. The trench conformed to the regulation specified in DVD forum specification "DVD-R for General, Physical Specification ver. 2.0" and had a maximum absorptive wavelength absorbance of 0.52 when measured by Lambda 25 UV/vis Spectrometer manufactured by Perkin Elmer. The spin-coated substrate was placed in a heat circulation oven at a temperature of 80° C. for 20 minutes to remove solvent contained therein to form a dye layer. Then an Ag film having a thickness of 100 nm was formed on the dye layer by sputtering (Swivel Sputter, manufactured by Balzers Co.) (Ag target: manufactured by Solar Applied Materials Technology Corp., Taiwan). On the inner periphery of the circular substrate was evenly coated with 1 g of UV curable acrylic adhesive (Product Cat. No. SD-698, manufactured by Dainippon Ink and Chemicals Incorporated, DIC) and then covered with a circular transparent polycarbonate substrate having a diameter of 120 mm and a thickness of 0.6 mm. The substrate was accelerative spun to 3000 rpm for 5 seconds and the acrylic resin was cured by illuminating UV lamp (Product Cat. No. UVM-201, manufactured by Hanky Corporation, Taiwan) to form a disc having a bonding layer.

Certain information was recorded on the disc by using DVD Tester ODU-1000 (wavelength 660 nm, NA 0.60) at a linear speed of 56 m/s (16-× DVD-R based linear speed) by a power of from 30 mW to 50 mW and then scanned the information recorded on the disc at a linear speed of 3.49 m/s. The lower jitter value is, the better the recording power is. The results were summarized in Table 1.

Experimental Example 2

A recording medium was prepared by following the procedures recited in Experimental Example 1 except that the amount of Compound No. 1 and No. 14 were both changed to 0.5 g (weight ratio of Compound No. 1 to Compound No. 14 was 50:50).

The resultant recording medium was elevated the same as in Experimental Example 1 and the results were summarized in Table 1.

Experimental Example 3

A recording medium was prepared by following the procedures recited in Experimental Example 1 except that the amount of Compound No. 1 and No. 14 were changed to 0.7 g and 0.3 g, respectively (weight ratio of Compound No. 1 to Compound No. 14 was 70:30).

The resultant recording medium was elevated the same as in Experimental Example 1 and the results were summarized in Table 1.

Experimental Example 4

A recording medium was prepared by following the procedures recited in Experimental Example 1 except that the Compound No. 1 was instead of Compound No. 8 in an amount of 0.3 g and the amount of the Compound No. 14 was changed to 0.7 g (weight ratio of Compound No. 5 to Compound No. 14 was 30:70).

The resultant recording medium was elevated the same as in Experimental Example 1 and the results were summarized in Table 1.

Experimental Example 5

A recording medium was prepared by following the procedures recited in Experimental Example 1 except that the Compound No. 1 was instead of Compound No. 5 in an amount of 0.5 g and the amount of the Compound No. 14 was changed to 0.5 g (weight ratio of Compound No. 5 to Compound No. 14 was 50:50).

The resultant recording medium was elevated the same as in Experimental Example 1 and the results were summarized in Table 1.

Experimental Example 6

A recording medium was prepared by following the procedures recited in Experimental Example 1 except that the Compound No. 1 was instead of Compound No. 5 in an amount of 0.7 g and the amount of the Compound No. 14 was changed to 0.3 g (weight ratio of Compound No. 5 to Compound No. 14 was 70:30).

The resultant recording medium was elevated the same as in Experimental Example 1 and the results were summarized in Table 1.

Comparative Experimental Example 1

A recording medium was prepared by following the procedures recited in Experimental Example 1 except that the dye solution was prepared by adding 1 g of Compound No. 45 into 90 g of 1,1,2,2-tetrafluoropropanol, stirring the solution at room temperature for 4 hours, and filtering the solution via a Teflon filter membrane having a pore size of 100 nm.

The resultant recording medium was elevated the same as in Experimental Example 1 and the results were summarized in Table 1.

TABLE 1

Compound No. 45

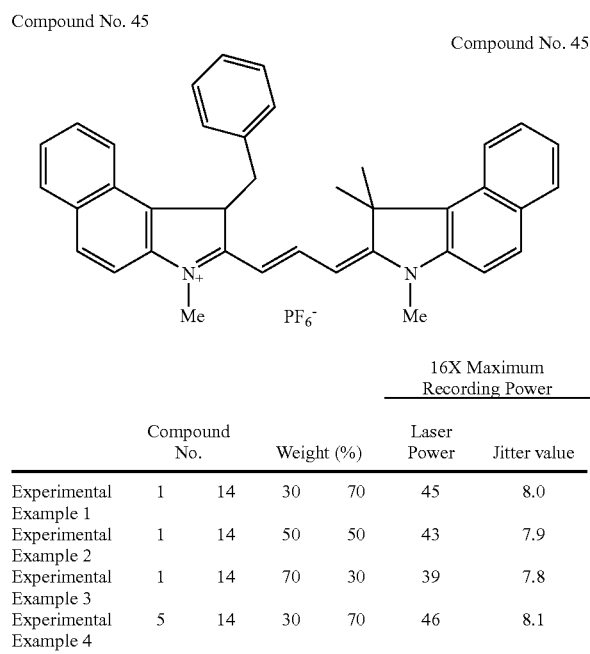

Compound No. 45

| | Compound No. | Weight (%) | | 16X Maximum Recording Power | |
|---|---|---|---|---|---|
| | | | | Laser Power | Jitter value |
| Experimental Example 1 | 1 | 14 | 30 | 70 | 45 | 8.0 |
| Experimental Example 2 | 1 | 14 | 50 | 50 | 43 | 7.9 |
| Experimental Example 3 | 1 | 14 | 70 | 30 | 39 | 7.8 |
| Experimental Example 4 | 5 | 14 | 30 | 70 | 46 | 8.1 |

TABLE 1-continued

Compound No. 45

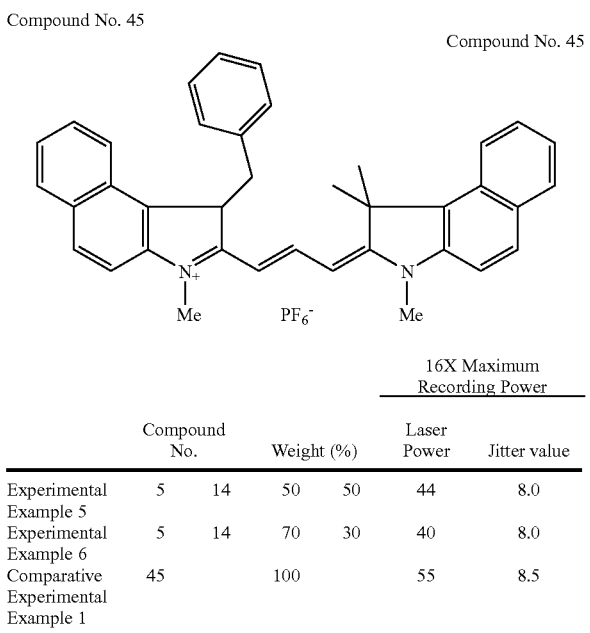

Compound No. 45

| | Compound No. | Weight (%) | | 16X Maximum Recording Power | |
|---|---|---|---|---|---|
| | | | | Laser Power | Jitter value |
| Experimental Example 5 | 5 | 14 | 50 | 50 | 44 | 8.0 |
| Experimental Example 6 | 5 | 14 | 70 | 30 | 40 | 8.0 |
| Comparative Experimental Example 1 | 45 | | 100 | | 55 | 8.5 |

It is to be understood that, although the invention has been described in conjunction with the detailed description thereof, the foregoing description is intended to be illustrative and not to limit the scope of the invention, which is defined by the scope of the appended claims. Other aspects, advantages and modifications are within the scope of the following claims.

What is claimed is:

1. A trimethine cyanine compound represented by the formula (1):

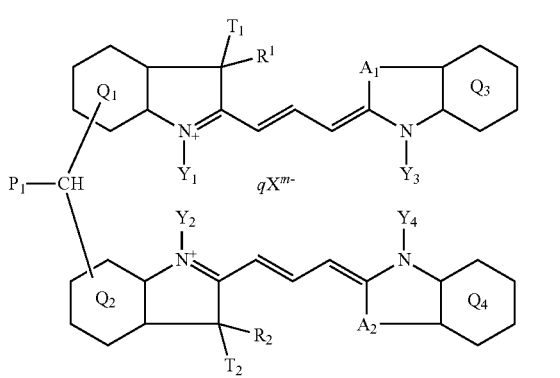

(1)

wherein:
Q$_1$, Q$_2$, Q$_3$, and Q$_4$ are the same or different and each represents a substituted or unsubstituted benzene ring or naphthalene ring;
P$_1$ is a hydrogen atom or an organic group having 1 to 18 carbon atoms;
A$_1$ and A$_2$ are the same or different and each represents groups of formula >CR$_3$R$_4$, >NR$_5$, an oxygen atom, or a sulfur atom;
Y$_1$, Y$_2$, Y$_3$, and Y$_4$ are the same or different and each represents an organic group having 1 to 18 carbon atoms;

T₁ and T₂ are the same or different and each represents a substituted or unsubstituted benzyl group, a substituted or unsubstituted allyl group, or a substituted or unsubstituted propargyl group;

R₁, R₂, R₃, R₄, and R₅ are the same or different and each represents a hydrocarbon group having 1-18 carbon atoms, which is substituted or unsubstituted; or R₃ and R₄ is bonded together to form a 3- to 6-member carbon ring which is further optionally fused with a benzene ring;

$X^{m-}$ represents a counterion having m valence;

m represents an integral of 1, 2, or 3;

q represents a coefficient for maintaining charge neutrality.

2. The trimethine cyanine compound according to claim 1, which is the compound represented by the following formula (2):

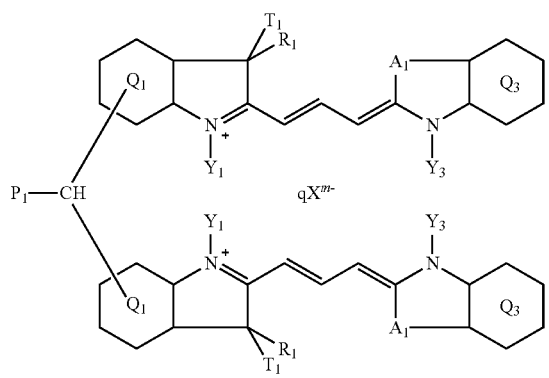

(2)

wherein $Q_1$, $Q_3$, $P_1$, $A_1$, $Y_1$, $Y_3$, $T_1$, $R_1$, $X^{m-}$, m and q are defined the same as in claim 1.

3. The trimethine cyanine compound according to claim 2, which is the compound represented by the following formula (4):

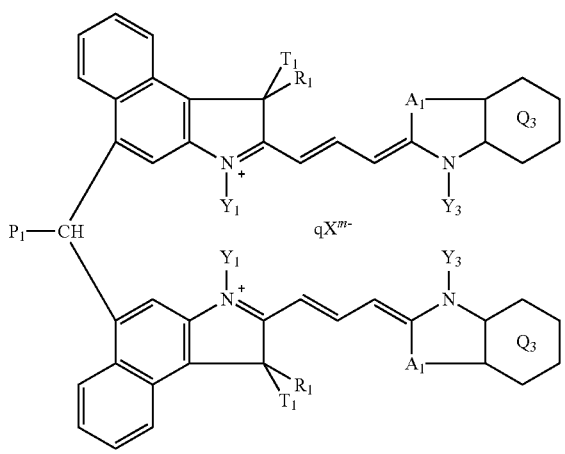

(4)

wherein $Q_1$, $P_1$, $A_1$, $Y_1$, $Y_3$, $T_1$, $R_1$, $X^{m-}$, m and q are defined the same as in claim 1.

4. An indolium compound represented by the following formula (8):

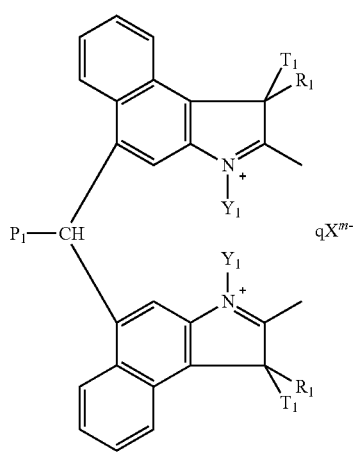

(8)

wherein:

P₁ is a hydrogen atom or an organic croup having 1 to 18 carbon atoms;

Y₁ represents an organic group having 1 to 18 carbon atoms;

T₁ represents a substituted or unsubstituted benzyl group, a substituted or unsubstituted allyl group, or a substituted or unsubstituted propargyl group;

R₁ represents a hydrocarbon group having 1-18 carbon atoms, which is substituted or unsubstituted;

$X^{m-}$ represents a counterion having m valence;

m represents an integral of 1, 2, or 3;

q represents a coefficient for maintaining charge neutrality.

5. A pseudo-indolium compound represented by the following formula (12):

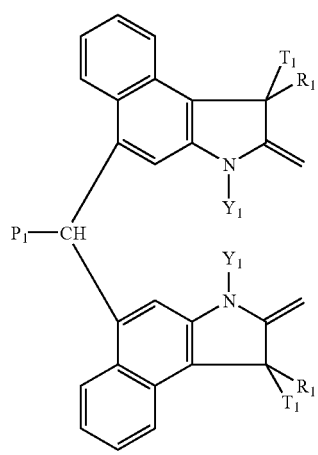

(12)

wherein:

P₁ is a hydrogen atom or an organic group having 1 to 18 carbon atoms;

Y₁ represents an organic group having 1 to 18 carbon atoms;

T₁ represents a substituted or unsubstituted benzyl group, a substituted or unsubstituted allyl group, or a substituted or unsubstituted propargyl group;

$R_1$ represents a hydrocarbon group having 1-18 carbon atoms, which is substituted or unsubstituted.

6. An optical recording material for forming an optical recording layer, which contains the trimethine cyanine compound according to any one claim of claims 1, 2 or 3.

7. An optical recording media, which comprises a substrate and an optical recording layer formed on the substrate, wherein the optical recording layer is a film prepared from the optical recording material according to claim 6.

\* \* \* \* \*